(12) United States Patent
Okumura (10) Patent No.: US 10,918,349 B2
(45) Date of Patent: Feb. 16, 2021

(54) MOBILE X-RAY IMAGING DEVICE

(71) Applicant: SHIMADZU CORPORATION, Kyoto (JP)

(72) Inventor: Hiroshi Okumura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 318 days.

(21) Appl. No.: 16/305,892

(22) PCT Filed: Jun. 1, 2016

(86) PCT No.: PCT/JP2016/066117
§ 371 (c)(1),
(2) Date: Nov. 30, 2018

(87) PCT Pub. No.: WO2017/208380
PCT Pub. Date: Dec. 7, 2017

(65) Prior Publication Data
US 2020/0315560 A1 Oct. 8, 2020

(51) Int. Cl.
*A61B 6/00* (2006.01)
*H02M 3/04* (2006.01)

(52) U.S. Cl.
CPC .......... *A61B 6/4405* (2013.01); *A61B 6/461* (2013.01); *A61B 6/48* (2013.01); *A61B 6/56* (2013.01); *H02M 3/04* (2013.01)

(58) Field of Classification Search
CPC .......... A61B 6/4405; A61B 6/56; A61B 6/48; A61B 6/461; H02M 3/04
USPC ......................................................... 378/62
See application file for complete search history.

(56) References Cited

U.S. PATENT DOCUMENTS

| | | | |
|---|---|---|---|
| 2012/0008748 | A1 | 1/2012 | Fuse et al. |
| 2013/0223596 | A1 | 8/2013 | Kojima et al. |
| 2014/0098939 | A1 | 4/2014 | Yamanaka |
| 2015/0312999 | A1 | 10/2015 | Takahashi et al. |

FOREIGN PATENT DOCUMENTS

| | | |
|---|---|---|
| JP | 2014073309 | 4/2014 |
| JP | 2014204783 | 10/2014 |
| JP | 2016067525 | 5/2016 |

OTHER PUBLICATIONS

"Office Action of Japan Counterpart Application", dated Apr. 7, 2020, with English translation thereof, p. 1-p. 6.
(Continued)

*Primary Examiner* — David P Porta
*Assistant Examiner* — Gisselle M Gutierrez
(74) *Attorney, Agent, or Firm* — JCIPRNET (57) ABSTRACT

In a first scenario, a third switch is opened when a first switch is opened to turn off the power supply provided to a device main body and a second switch is short-circuited. The third switch is opened as a result of the power supply provided to the main body controller being stopped. In a second scenario, the third switch is opened when the device main body is in a running state, the first and second switches are short-circuited, when a trolley is moved between hospital rooms. Whether or not the device main body is in a running state is recognized as a result of a lock unit sending a signal to the main body controller, said signal indicating that an arm has come in contact with the lock unit and the arm is arranged at a fixed position where the arm should be arranged when moving the trolley.

7 Claims, 5 Drawing Sheets

(56) References Cited

OTHER PUBLICATIONS

"Office Action of Japan Counterpart Application," with English translation thereof, dated Sep. 17, 2019, p. 1- p. 6.
"Search Report of Europe Counterpart Application", dated Dec. 12, 2019, p. 1-p. 11.
"International Search Report (Form PCT/ISA/210)" of PCT/JP2016/066117, dated Aug. 16, 2016, with English translation thereof, pp. 1-4.
"Written Opinion of the International Searching Authority (Form PCT/ISA/237)" of PCT/JP2016/066117, dated Aug. 16, 2016, with English translation thereof, pp. 1-6.

MOBILE X-RAY IMAGING DEVICE

CROSS-REFERENCE TO RELATED APPLICATION

This application is a 371 application of the International PCT application serial no. PCT/JP2016/066117, filed on Jun. 1, 2016. The entirety of each of the above-mentioned patent applications is hereby incorporated by reference herein and made a part of this specification.

TECHNICAL FIELD

The present invention relates to a mobile X-ray imaging device.

BACKGROUND ART

Such a mobile X-ray imaging device is also called a portable X-ray imaging device, and has a trolley on which wheels are disposed in order to move between hospital rooms, and has a configuration in which X-rays are emitted from an X-ray tube supported by a support member and of which an emission field is regulated by a collimator are emitted to a subject, and X-rays that have passed through the subject are captured by using a film. In such a mobile X-ray imaging device, a battery for applying a high voltage to the X-ray tube is mounted in the trolley so that an X-ray imaging can be performed in unspecified places where there is no external power supply.

In recent years, a mobile X-ray imaging device including a digital type X-ray detector such as a flat panel detector in place of a film has been increasingly used. Such an X-ray imaging device is also called a digital radiographic (DR) device, and has a configuration in which an image captured by an X-ray detector such as a flat panel detector (FPD) can be displayed immediately on a display unit such as a liquid crystal display (LCD). In such a DR type mobile X-ray imaging device, a power is supplied from the battery to not only the X-ray tube but also the flat panel detector and the LCD (refer to Patent Literature 1).

CITATION LIST

Patent Literature

Patent Literature 1: Japanese Unexamined Patent Application Publication No. 2014-204783

SUMMARY OF INVENTION

Technical Problem

In the related art, a film type mobile X-ray imaging device and a DR type mobile X-ray imaging device have the same configuration except for the provision of a flat panel detector, a display unit, or a controller thereof. Therefore, in such a mobile X-ray imaging device, parts other than the flat panel detector and the display unit are produced as common components, and when a DR type is used, the device is produced in a form in which the flat panel detector, the display device, and the controller thereof are attached to the common components. Therefore, it is possible to reduce costs according to component commonization.

Figure 5:
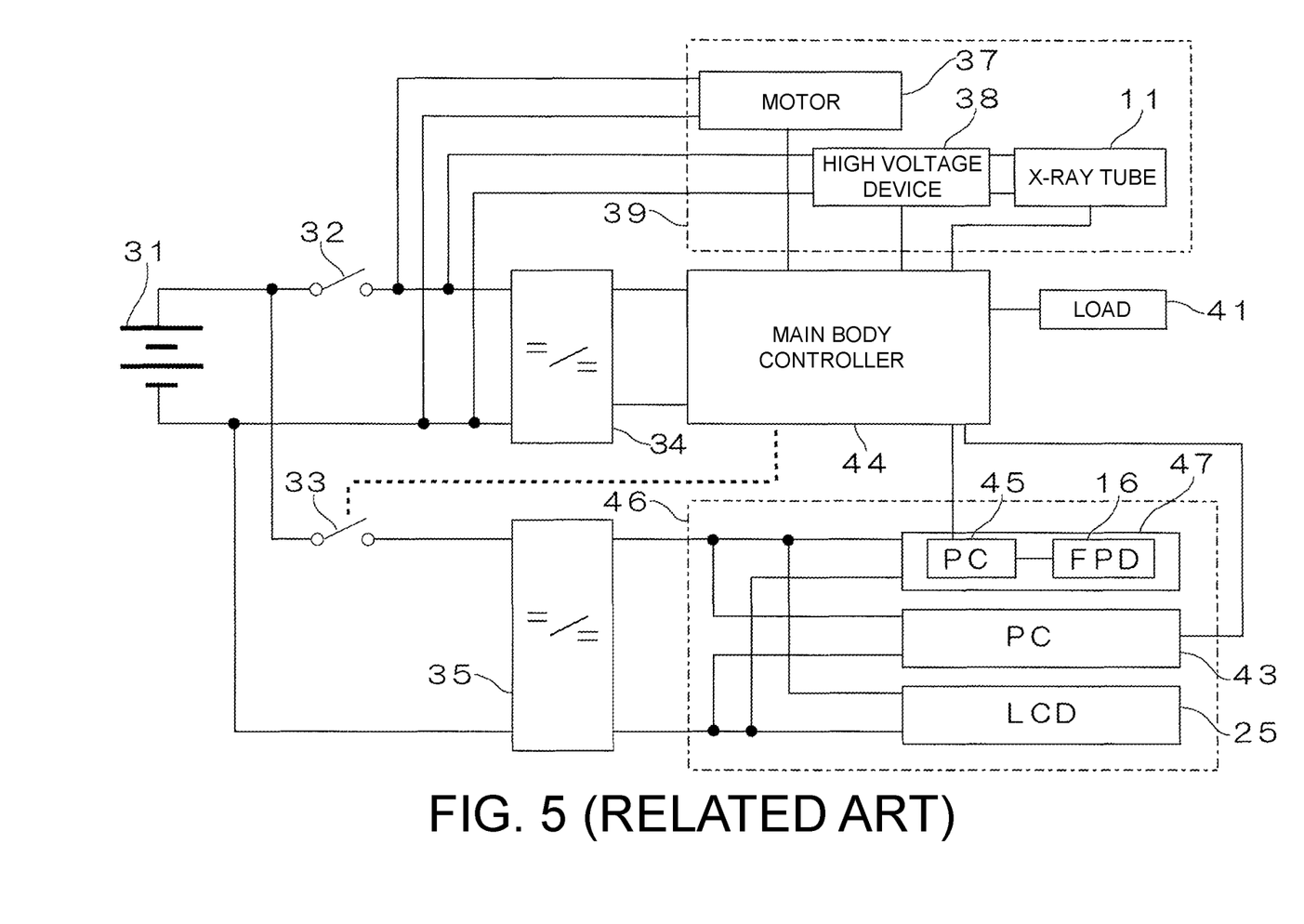
FIG. 5 is a block diagram of a mobile X-ray imaging device having a configuration in which device main body parts other than a flat panel detector and a display unit are produced as common components, and a flat panel detector, a display device, and a controller thereof are then attached to the common components.

FIG. 5 is a block diagram of a mobile X-ray imaging device having a configuration in which device main body parts other than a flat panel detector and a display unit are produced as common components, and a flat panel detector, a display device, and a controller thereof are then attached to the common components.

The mobile X-ray imaging device includes a main body controller 44 that includes a processor and controls the entire device. The main body controller 44 is connected to an X-ray tube 11 and a high voltage device 38 for applying a high voltage to the X-ray tube 11. In addition, the main body controller 44 is connected to a motor 37 as a drive source for moving the device.

In addition, the mobile X-ray imaging device includes a battery 31. The battery 31 can supply, for example, a direct current (DC) of 240 V (volts). The battery 31 is connected to the main body controller 44 through the main body DC-DC converter 34 for changing a voltage of the battery 31 to, for example, a voltage of about 15 V, for supply to the main body controller 44. A switch 32 for opening or closing a power supply path from the battery 31 to the main body controller 44 through the main body DC-DC converter 34 is disposed between the main body DC-DC converter 34 and the battery 31.

Here, a high load unit 39 composed of the high voltage device 38, the X-ray tube 11, and the motor 37 directly receives a direct current of 240 V from the battery 31 without passing through the main body DC-DC converter 34. On the other hand, a small load 41 in the device main body is configured to receive a drive current through the main body controller 44.

In addition, a DR unit 46 is attached so that the mobile X-ray imaging device serves as a DR type imaging device. The DR unit 46 includes an X-ray detection unit 47 including a flat panel detector (FPD) 16 as an X-ray detector configured to detect X-rays that are emitted from the X-ray tube 11 and have passed through a subject and a flat panel detector controller 45 that is composed of a personal computer (PC) including a processor and controls the flat panel detector 16. In addition, the DR unit 46 includes a display unit 25 that is composed of an LCD (liquid crystal display) and displays a digital image detected by the flat panel detector 16. In addition, the DR unit 46 includes a DR unit controller 43 that is composed of a personal computer (PC) including a processor and controls the X-ray detection unit 47 and the display unit 25.

The DR unit 46 is provided additionally to the above common components. The DR unit 46 is connected to the battery 31 through a DR unit DC-DC converter 35 for changing a voltage of the battery 31 to, for example, a voltage of about 15 V, for supply to the X-ray detection unit 47, the display unit 25, and the DR unit controller 43 in the DR unit 46. A switch 33 for opening or closing a power supply path from the battery 31 to the DR unit 46 through the DR unit DC-DC converter 35 is disposed between the DR unit DC-DC converter 35 and the battery 31.

The main body controller 44 and the DR unit controller 43 are connected to transmit and receive a control signal. In addition, the main body controller 44 and the flat panel detector controller 45 in the X-ray detection unit 47 are connected to transmit and receive an X-ray exposure timing signal.

When the mobile X-ray imaging device is used, the switch 32 is short-circuited and thus a power is supplied from the battery 31 to the main body controller 44 through the main body DC-DC converter 34. Thereafter, the switch 33 is short-circuited, and thus power is supplied from the battery 31 to the DR unit 46 through the DR unit DC-DC converter 35.

In this manner, when a moving X-ray imaging device has a configuration in which parts other than the X-ray detection unit 47, the display unit 25, and the DR unit controller 43 are produced as common components, and then the DR unit 46 composed of the X-ray detection unit 47, the display unit 25, and the DR unit controller 43 is attached to the common components, it is possible to reduce costs according to component commonization.

On the other hand, when the DR unit 46 is attached to the common components, it is necessary for the battery 31 to supply power not only to the high load unit 39 and the main body controller 44 but also to the DR unit 46. Therefore, in order save power, it is necessary to minimize power used by the DR unit 46. Thus, for example, when X-ray imaging is not performed such as during moving between hospital rooms, preferably, the switch 33 is opened in response to a signal from the main body controller 44 according to an operation performed by an operator, thus power consumption in the DR unit 46 is prevented, and power consumption in the battery 31 is reduced.

However, there is a problem that, when the power supply provided to the DR unit 46 is stopped every time the device moves between hospital rooms, it takes a long time to shut down the DR unit controller 43 composed of a personal computer including a processor and it takes a long time to activate the DR unit controller 43. Therefore, in fact, the operation of stopping power supply provided to the DR unit 46 every time the device moves between hospital rooms is actually not employed. Therefore, there is a problem that the power consumption of the battery 31 increases due to attachment of the DR unit 46.

The present invention has been made in order to solve the above problems, and an objective of the present invention is to provide a mobile X-ray imaging device having a configuration in which a DR unit is provided additionally to common components and in which power consumption of battery can be reduced when an X-ray detection unit is not used such as during moving between hospital rooms.

Solution to Problem

In the disclosure, a mobile X-ray imaging device includes a device main body including a trolley and an X-ray tube that is supported on the trolley through a support member; a battery that is mounted in the device main body; a main body controller that includes a processor and controls the device main body; a DR unit that includes an X-ray detector configured to detect X-rays that are emitted from the X-ray tube and have passed through a subject, an X-ray detection unit including an X-ray detector controller that includes a processor and controls the X-ray detector, a display unit configured to display an image detected by the X-ray detector, and a DR unit controller that includes a processor and controls the X-ray detection unit and the display unit; a main body DC-DC converter that changes a voltage of the battery to a voltage supplied to the main body controller; a DR unit DC-DC converter that changes a voltage of the battery to a voltage supplied to the X-ray detection unit, the display unit, and the DR unit controller in the DR unit; a first switch that opens or closes a power supply path from the battery to the main body controller through the main body DC-DC converter; a second switch that opens or closes a power supply path from the battery to the DR unit through the DR unit DC-DC converter; and a third switch that opens or closes a power supply path to the X-ray detection unit.

In the disclosure, the DR unit DC-DC converter is disposed between the battery and the X-ray detection unit, the display unit, and the DR unit controller in the DR unit, and the third switch opens or closes a power supply path from the DR unit DC-DC converter to the X-ray detection unit.

In the disclosure, the DR unit DC-DC converter is composed of a first DR unit DC-DC converter disposed between the battery and the display unit and the DR unit controller in the DR unit and a second DR unit DC-DC converter disposed between the battery and the X-ray detection unit in the DR unit, and the third switch opens or closes a power supply path from the battery to the X-ray detection unit through the second DR unit DC-DC converter.

In the disclosure, the third switch is opened when the first switch is opened and the second switch is short-circuited.

In the disclosure, the third switch is a make contact relay that is driven by power supplied to the main body controller.

In the disclosure, the mobile X-ray imaging device further includes a detection unit configured to detect whether the device main body is in a running state, and the third switch is opened when the first switch and the second switch are short-circuited and the device main body is in a running state.

In the disclosure, the third switch is opened after the main body controller receives a third switch opening permission signal from the DR unit controller.

Advantageous Effects of Invention

In the disclosure, when the third switch is opened, the power supply provided to the X-ray detection unit can be stopped while the power supply provided to the display unit and the DR unit controller in the DR unit continues. Therefore, it is possible to reduce power consumption in the battery. In this case, according to a configuration including a DR unit DC-DC converter separately from a main body DC-DC converter, the mobile X-ray imaging device can be produced by providing a DR unit in addition to the common components, and it is possible to reduce the device costs.

According to the invention of claim 1, In the disclosure, when the power supply provided to the device main body is turned off and the power supply provided to the display unit and the DR unit controller in the DR unit continues, the power supply provided to the X-ray detection unit can be stopped and it is possible to reduce power consumption in the battery.

In the disclosure, when power is not supplied to the main body DC-DC converter due to an operation of the make contact relay, the third switch can be opened.

In the disclosure, when the device main body is in a running state and X-ray imaging is not being performed and the power supply provided to the display unit and the DR unit controller in the DR unit continues, the power supply provided to the X-ray detection unit can be stopped and it is possible to reduce power consumption in the battery.

In the disclosure, after the DR unit controller confirms that an operation is completed, the third switch can be opened.

DESCRIPTION OF EMBODIMENTS

Figure 1:
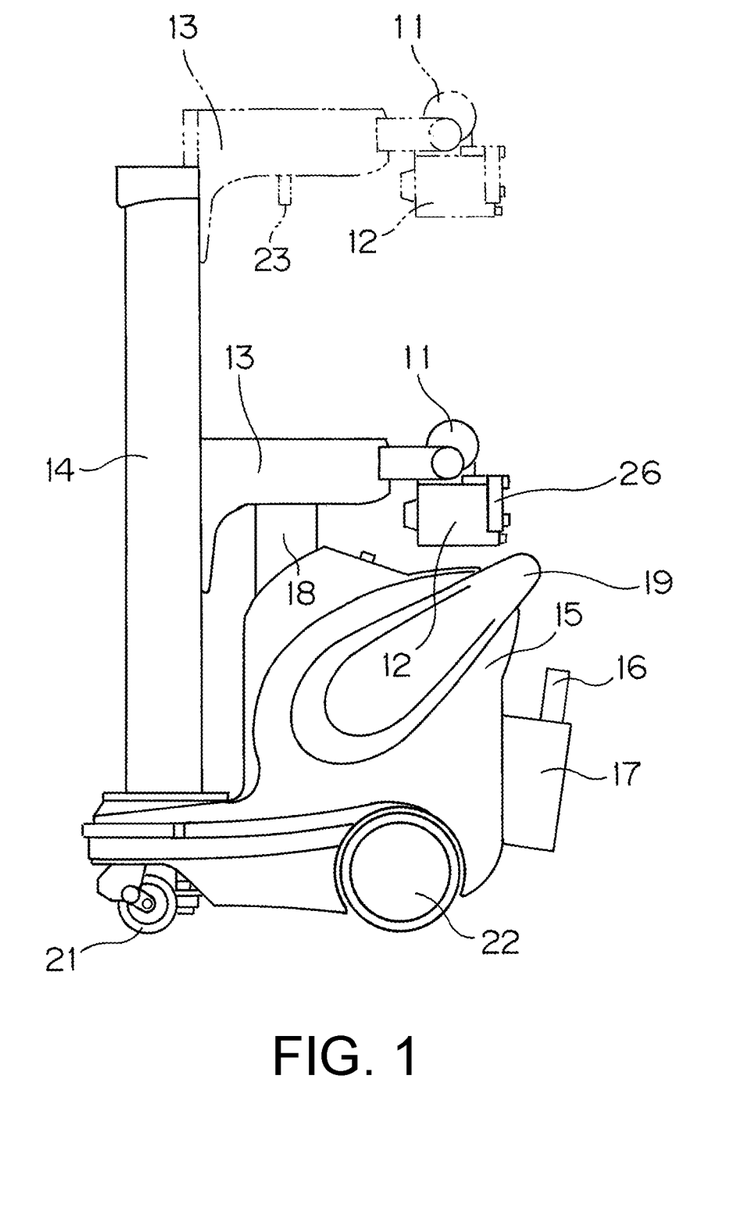
FIG. 1 is a schematic side view of a mobile X-ray imaging device according to the present invention.
Figure 2:
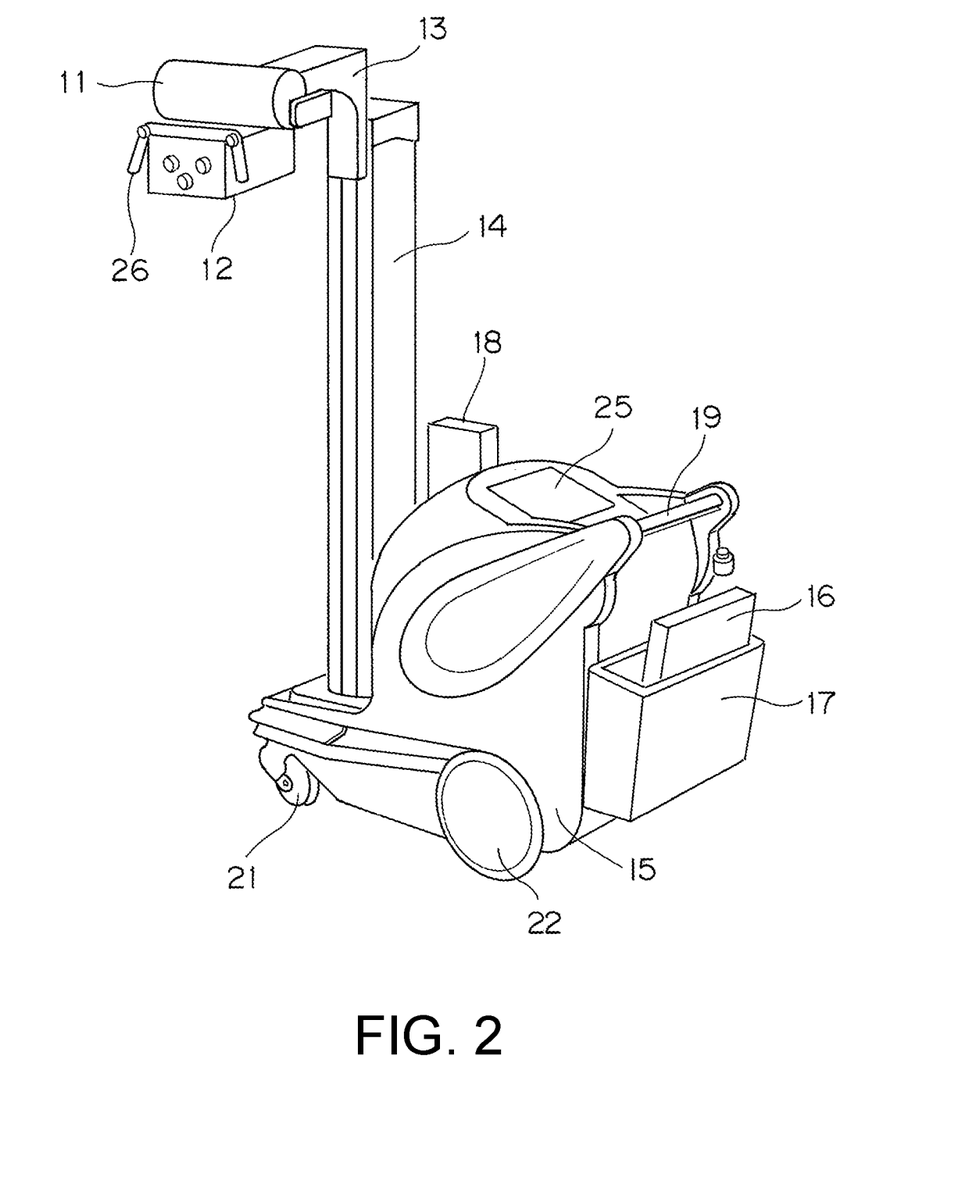
FIG. 2 is a perspective view of the mobile X-ray imaging device according to the present invention.

Embodiments of the present invention will be described below with reference to the drawings. FIG. 1 is a schematic side view of a mobile X-ray imaging device according to the present invention. In addition, FIG. 2 is a perspective view of the mobile X-ray imaging device according to the present invention.

The mobile X-ray imaging device is also called a portable X-ray imaging device and moves between a plurality of hospital rooms, and performs X-ray imaging in the hospital rooms. This X-ray imaging device includes a support column 14 disposed on a trolley 15, an arm 13 disposed in such a manner that it is elevatable with respect to the support column 14, an X-ray tube 11 disposed at the tip of the arm 13, a collimator 12 disposed below the X-ray tube 11, a handle 26 attached to the collimator 12, a flat panel detector 16 as an X-ray detector for detecting X-rays that are emitted from the X-ray tube 11 and have passed through a subject, and a storage unit 17 in which the flat panel detector 16 is accommodated.

In addition, the mobile X-ray imaging device includes a display unit for a digital image detected by the flat panel detector 16 and a display unit 25 composed of a touch panel type LCD functioning as an input unit for a DR unit 46 (to be described below). In addition, the mobile X-ray imaging device includes a pair of left and right front wheels 21 which are wheels for direction change, a pair of left and right rear wheels 22 which are wheels for driving, and an operation handle 19 for handing a direction of travel of the trolley 15. The rear wheels 22 are rotated when a motor 37 (to be described below) is driven.

The arm 13 can move up and down between a fixed position which is a position at which the arm 13 will be disposed when the trolley 15 is moved and an imaging position raised from the fixed position, as indicated by a solid line in FIG. 1. When the arm 13 is at the fixed position, the bottom surface of the arm 13 abuts a lock unit 18 called an arm catch. In this state, a pin 23 disposed on the bottom surface of the arm 13 is accommodated in a hole (not shown) formed in the lock unit 18. In addition, as shown in FIG. 2, the arm 13 turns around the support column 14 while it is raised from the fixed position.

Figure 3:
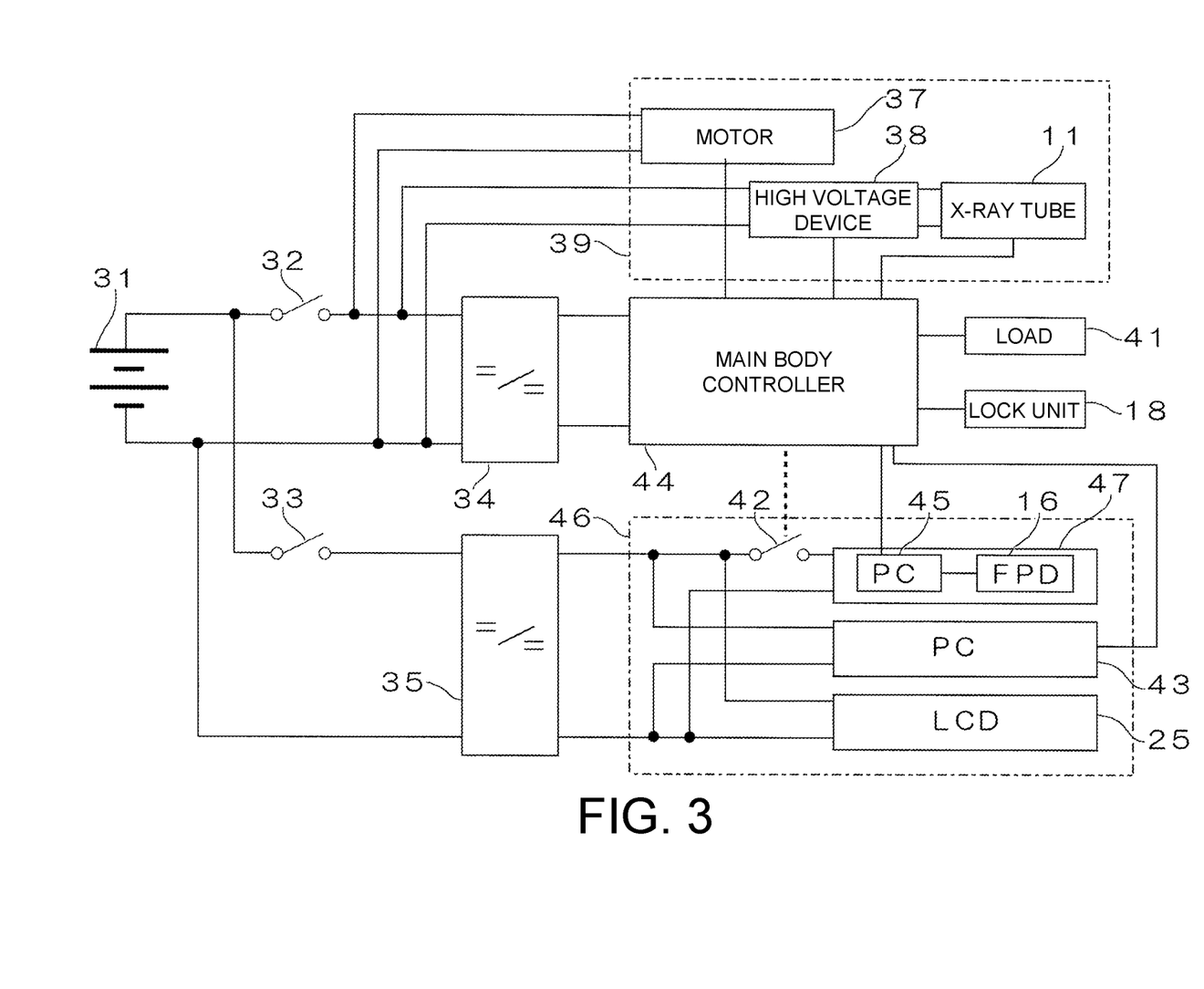
FIG. 3 is a block diagram of a mobile X-ray imaging device according to a first embodiment of the present invention.

FIG. 3 is a block diagram of a mobile X-ray imaging device according to a first embodiment of the present invention. Here, like the mobile X-ray imaging device shown in FIG. 5, this mobile X-ray imaging device has a configuration in which device main body parts other than the flat panel detector 16 and the display unit 25 are produced as common components, and the DR unit 46 including an X-ray detection unit 47 including the flat panel detector 16, the display unit 25 configured to display a digital image and the like, and a DR unit controller 43 that controls them is then attached to the common components. Here, components the same as the components shown in FIG. 5 will be denoted with the same reference numerals.

The mobile X-ray imaging device includes a main body controller 44 that includes a processor and controls the entire device. The main body controller 44 is connected to the X-ray tube 11 and a high voltage device 38 for applying a high voltage to the X-ray tube 11. In addition, the main body controller 44 is connected to the motor 37 as a drive source for driving the above rear wheels 22 and moving the device. In addition, the main body controller 44 is connected to the above lock unit 18 and the main body controller 44 can detect that the arm 13 is in a fixed state.

In addition, the mobile X-ray imaging device includes a battery 31. The battery 31 can supply, for example, a direct current of 240 V. The battery 31 is connected to the main body controller 44 through a main body DC-DC converter 34 for changing a voltage of the battery 31 to, for example, a voltage of about 15 V, for supply to the main body controller 44. A first switch 32 for opening or closing a power supply path from the battery 31 to the main body controller 44 through the main body DC-DC converter 34 is disposed between the main body DC-DC converter 34 and the battery 31.

Here, a high load unit 39 composed of the high voltage device 38, the X-ray tube 11, and the motor 37 directly receives a direct current of 240 V from the battery 31 without passing through the main body DC-DC converter 34. On the other hand, a small load 41 in the device main body is configured to receive a drive current through the main body controller 44. Here, the load 41 includes, for example, an operation panel for performing operations of the device main body part.

In addition, the DR unit 46 is attached so that the mobile X-ray imaging device serves as a DR type imaging device. The DR unit 46 includes the X-ray detection unit 47 including the flat panel detector 16 and a flat panel detector controller 45 that is composed of a personal computer including a processor and controls the flat panel detector 16. In addition, the DR unit 46 includes the display unit 25 that is composed of an LCD and displays a digital image detected by the flat panel detector 16. In addition, the DR unit 46 includes the DR unit controller 43 that is composed of a personal computer including a processor and controls the X-ray detection unit 47 and the display unit 25.

Here, the flat panel detector 16 and the flat panel detector controller 45 in the X-ray detection unit 47 are connected via a wire. However, the flat panel detector 16 and the flat panel detector controller 45 in the X-ray detection unit 47 may be connected wirelessly. When the flat panel detector 16 and the flat panel detector controller 45 in the X-ray detection unit 47 are wirelessly connected, an access point is attached to the flat panel detector controller 45, and the flat panel detector 16 and the flat panel detector controller 45 are connected to each other via the access point.

The DR unit 46 is provided additionally to the above common components. The DR unit 46 is connected to the battery 31 through a DR unit DC-DC converter 35 for changing a voltage of the battery 31 to, for example, a voltage of about 15 V, for supply to the X-ray detection unit 47, the display unit 25, and the DR unit controller 43 in the DR unit 46. A second switch 33 for opening or closing a power supply path from the battery 31 to the DR unit 46 through the DR unit DC-DC converter 35 is disposed between the DR unit DC-DC converter 35 and the battery 31.

In addition, a third switch 42 for opening or closing a power supply path to the X-ray detection unit is disposed between the DR unit DC-DC converter 35 and the X-ray detection unit 47. The third switch 42 is opened or closed in response to an instruction from the main body controller 44. The third switch 42 is composed of a make contact relay that is driven by power supplied to the main body controller 44. The make contact is a contact which is also referred to as an arbeit contact (a contact) or a normally open contact, and is a contact that blocks the circuit when it operates and opens a circuit when the power is not supplied.

The main body controller 44 and the DR unit controller 43 are connected to transmit and receive a control signal. In addition, the main body controller 44 and the flat panel detector controller 45 in the X-ray detection unit 47 are connected to transmit and receive an X-ray exposure timing signal.

When the mobile X-ray imaging device is used, the first switch 32 is short-circuited and thus power is supplied from the battery 31 to the main body controller 44 through the main body DC-DC converter 34. Thereafter, the second switch 33 is short-circuited, and thus power is supplied from the battery 31 to the DR unit 46 through the DR unit DC-DC converter 35. In this case, the third switch 42 is short-circuited.

In this state, power of the battery 31 is consumed by the main body controller 44 including a processor. In addition, power of the battery 31 is consumed also in the load 41 including an operation panel connected to the main body controller 44. In addition, in the DR unit 46, power of the battery 31 is consumed in the flat panel detector 16 and the flat panel detector controller 45 composed of a personal computer including a processor. In addition, in the DR unit 46, power of the battery 31 is consumed in the DR unit controller 43 that is composed of a personal computer including a processor and controls the X-ray detection unit 47 and the display unit 25. In addition, when an image and the like are displayed on the display unit 25, the power of the battery 31 is also consumed in the display unit 25.

Therefore, in the mobile X-ray imaging device according to the present invention, when X-ray imaging using the flat panel detector 16 is not performed, the third switch 42 is opened in response to an instruction from the main body controller 44 and thus power consumption in the X-ray detection unit 47 is stopped.

More specifically, as a first case, the first switch 32 is opened in order to turn off the power supply provided to the device main body or bring it to a sleep state, and when the second switch 33 is short-circuited, the third switch 42 is opened in response to an instruction from the main body controller 44. That is, when the power supply provided to the main body controller 44 is stopped, the third switch 42 composed of a make contact relay is opened. In this state, since the power supply provided to the main body controller 44 is stopped and X-ray imaging is not performed, the third switch 42 is opened, and power consumption in the flat panel detector 16 and the flat panel detector controller 45 in the X-ray detection unit 47 is prevented.

In this state, since the second switch 33 is short-circuited, still, in the DR unit 46, the power supply provided to the DR unit controller 43 composed of a personal computer including a processor and the display unit 25 continues. Therefore, no particular time is required for shut down or activation of the DR unit controller 43. On the other hand, it is possible to reduce power consumption of the battery 31 in a situation in which the power supply provided to the device main body is in an off state or a sleep state and the X-ray detection unit 47 is not used.

As a second case, when the trolley 15 shown in FIG. 1 is moved between hospital rooms or the like, while the first switch 32 is short-circuited and the second switch 33 is short-circuited, if the device main body is in a running state, the third switch 42 is opened. Whether the device main body is in a running state is determined by the lock unit 18 transmitting a signal indicating that the arm 13 is disposed at a fixed position that is a position at which the arm 13 will be disposed when the trolley 15 is moved, as indicated by a solid line in FIG. 1, to the main body controller 44 when the bottom surface of the arm 13 abuts the lock unit 18 called an arm catch and the pin 23 disposed on the bottom surface of the arm 13 is accommodated in a hole formed at the lock unit 18.

In this state, the mobile X-ray imaging device including the trolley 15 moves when the motor 37 is driven. In this case, the third switch 42 is opened. That is, since X-ray imaging is not performed during moving of the device, the third switch 42 is opened and power consumption in the flat panel detector 16 and the flat panel detector controller 45 in the X-ray detection unit 47 is prevented.

In this state, since the second switch 33 is short-circuited, still, in the DR unit 46, the power supply provided to the DR unit controller 43 composed of a personal computer including a processor and the display unit 25 continues. Therefore, no particular time is required for shut down or activation of the DR unit controller 43 even when moving between hospital rooms. On the other hand, when the X-ray detection unit 47 is not used such as during moving between hospital rooms, it is possible to reduce power consumption of the battery 31.

Here, as described above, the fact that the device main body is in a running state is detected when the lock unit 18 transmits a signal indicating that the arm 13 is disposed at a fixed position that is a position at which the arm 13 will be disposed when the trolley 15 is moved to the main body controller 44. Instead of this, whether the device main body is in a running state may be detected by detecting rotation of the motor 37 or the like.

Here, in the above first and second cases, when the first switch 32 is opened and the second switch 33 is short-circuited or when the first switch 32 and the second switch 33 are short-circuited and the device main body is in a running state, an opening operation of the third switch 42 is preferably performed after the main body controller 44 receives a third switch opening permission signal from the DR unit controller 43. Therefore, for example, after the DR unit controller 43 confirms that an operation such as a process of transferring a digital image is completed, the third switch 42 can be opened.

As described above, in the mobile X-ray imaging device according to this embodiment, even if the DR unit 46 is provided additionally to the common components, when the X-ray detection unit 47 is not used such as during moving between hospital rooms, it is possible to reduce power consumption of the battery 31.

Figure 4:
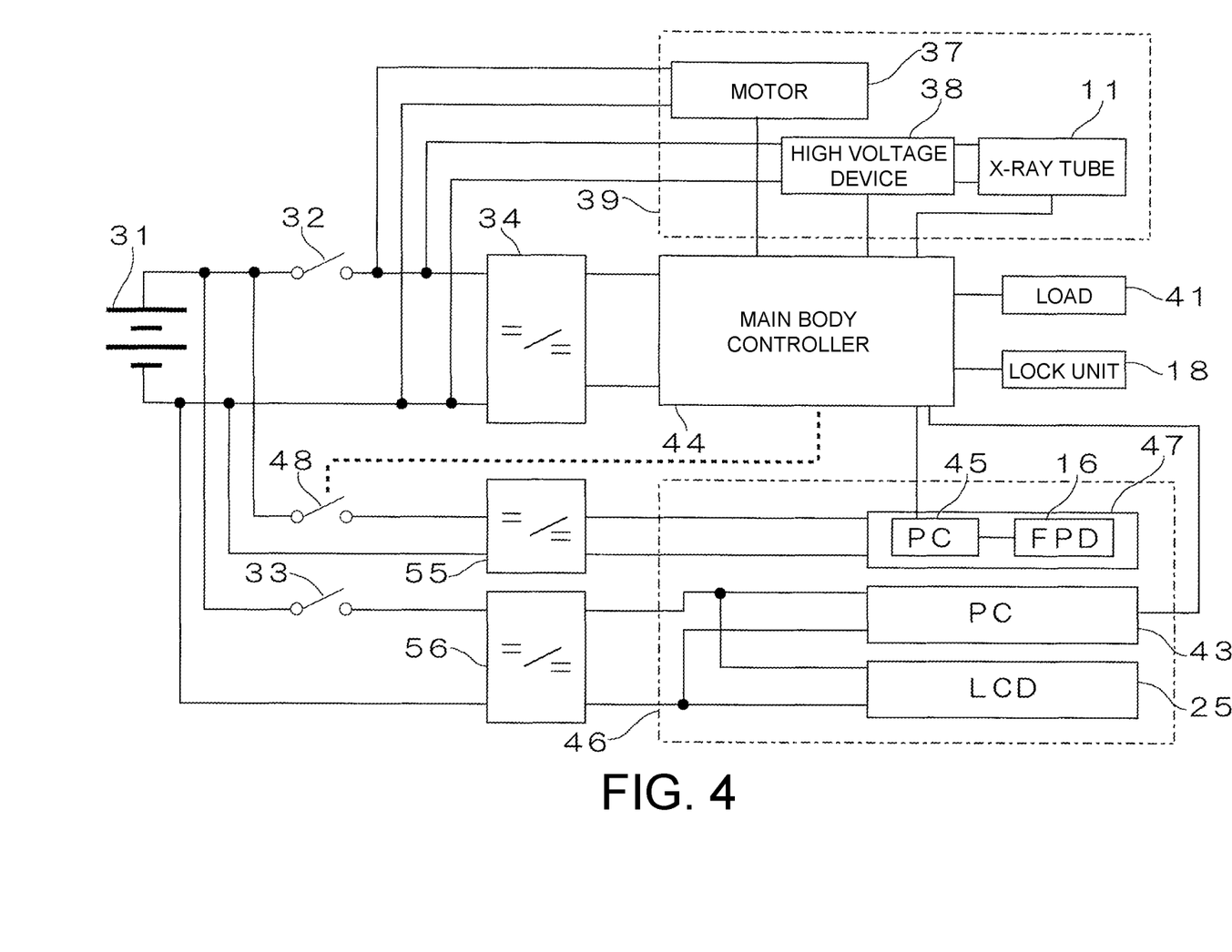
FIG. 4 is a block diagram of a mobile X-ray imaging device according to a second embodiment of the present invention.

Next, another embodiment of the present invention will be described. FIG. 4 is a block diagram of a mobile X-ray imaging device according to a second embodiment of the present invention. Like the mobile X-ray imaging device shown in FIG. 5, this mobile X-ray imaging device has a configuration in which device main body parts other than the flat panel detector 16 and the display unit 25 are produced as common components, and the DR unit 46 including an X-ray detection unit 47 including the flat panel detector 16, the display unit 25 configured to display a digital image and the like, and a DR unit controller 43 that controls them is then attached to the common components. Here, components the same as in the mobile X-ray imaging device according to the second embodiment shown in FIG. 6 will be denoted with the same reference numerals.

In the above first embodiment, power is supplied from the battery 31 to the X-ray detection unit 47, the display unit 25, and the DR unit controller 43 in the DR unit 46 through the DR unit DC-DC converter 35. On the other hand, in the second embodiment, a first DR unit DC-DC converter 56 disposed between the battery 31 and the display unit 25 and the DR unit controller 43 in the DR unit 46, and a second DR unit DC-DC converter 55 disposed between the battery 31 and the X-ray detection unit 47 in the DR unit 46 are provided. Power is supplied to the display unit 25 and the DR unit controller 43 through the first DR unit DC-DC converter 56, and power is supplied to the X-ray detection unit 47 through the second DR unit DC-DC converter 55.

Thus, the second switch 33 that opens or closes a power supply path from the battery 31 to the display unit 25 and the DR unit controller 43 in the DR unit 46 through the first DR unit DC-DC converter 56 is disposed between the battery 31 and the first DR unit DC-DC converter 56. In addition, a third switch 48 that opens or closes a power supply path from the battery 31 to the X-ray detection unit 47 of the DR unit 46 through the second DR unit DC-DC converter 55 is disposed between the battery 31 and the second DR unit DC-DC converter 55.

Like the third switch 42 according to the first embodiment, the third switch 48 opens or closes in response to an instruction from the main body controller 44 and is composed of a make contact relay that is driven by power supplied to the main body controller 44.

In the mobile X-ray imaging device according to the second embodiment, like the mobile X-ray imaging device according to the above first embodiment, as a first case, when the first switch 32 is opened to turn off the power supply provided to the device main body and the second switch 33 is short-circuited, the third switch 42 is opened in response to an instruction from the main body controller 44. That is, when the power supply provided to the main body controller 44 is stopped, the third switch 48 composed of a make contact relay is opened. In this state, since the power supply provided to the main body controller 44 is stopped and X-ray imaging is not performed, the third switch 42 is opened, and power consumption in the flat panel detector 16 and the flat panel detector controller 45 in the X-ray detection unit 47 is prevented. In addition, as a second case, when the trolley 15 shown in FIG. 1 is moved between hospital rooms or the like, while the first switch 32 is short-circuited and the second switch 33 is short-circuited, if the device main body is in a running state, the third switch 48 is opened.

Here, in the mobile X-ray imaging device according to the second embodiment, between the battery 31 and the second DR unit DC-DC converter 55, the third switch 48 that opens or closes a power supply path from the battery 31 to the X-ray detection unit 47 of the DR unit 46 through the second DR unit DC-DC converter 55 is disposed. However, the second DR unit DC-DC converter 55 and the third switch 48 may be integrated. That is, a configuration in which a power supply path from the battery 31 to the X-ray detection unit 47 of the DR unit 46 through the second DR unit DC-DC converter 55 is opened or closed using a DC-DC converter that can be controlled remotely in response to an instruction from the main body controller 44 may be used.

Likewise, the first switch and main body DC-DC converter 34 described above may be set as DC-DC converter that can be controlled remotely, and the second switch 33 and the DR unit DC-DC converter 35 may be set as a DC-DC converter that can be controlled remotely.

The invention claimed is:

1. A mobile X-ray imaging device comprising:
a device main body including a trolley and an X-ray tube that is supported on the trolley through a support member;
a battery that is mounted in the device main body;
a main body controller that includes a processor and controls the device main body;
a DR unit that includes an X-ray detection unit that includes an X-ray detector configured to detect X-rays that are emitted from the X-ray tube and have passed through a subject and an X-ray detector controller that includes a processor and controls the X-ray detector, a display unit configured to display an image detected by the X-ray detector, and a DR unit controller that includes a processor and controls the X-ray detection unit and the display unit;
a main body DC-DC converter that changes a voltage of the battery to a voltage supplied to the main body controller;
a DR unit DC-DC converter that changes a voltage of the battery to a voltage supplied to the X-ray detection unit, the display unit, and the DR unit controller in the DR unit;
a first switch that opens or closes a power supply path from the battery to the main body controller through the main body DC-DC converter;
a second switch that opens or closes a power supply path from the battery to the DR unit through the DR unit DC-DC converter; and
a third switch that opens or closes a power supply path to the X-ray detection unit.

2. The mobile X-ray imaging device according to claim 1, wherein the DR unit DC-DC converter is disposed between the battery and the X-ray detection unit, the display unit, and the DR unit controller in the DR unit, and
wherein the third switch opens or closes a power supply path from the DR unit DC-DC converter to the X-ray detection unit.

3. The mobile X-ray imaging device according to claim 1, wherein the DR unit DC-DC converter is composed of a first DR unit DC-DC converter disposed between the battery and the display unit and the DR unit controller in the DR unit and a second DR unit DC-DC converter disposed between the battery and the X-ray detection unit in the DR unit, and
wherein the third switch opens or closes a power supply path from the battery to the X-ray detection unit through the second DR unit DC-DC converter.

4. The mobile X-ray imaging device according to claim 1, wherein the third switch is opened when the first switch is opened and the second switch is short-circuited.

5. The mobile X-ray imaging device according to claim 4, wherein the third switch is a make contact relay that is driven by a power supplied to the main body controller.

6. The mobile X-ray imaging device according to claim 1, comprising
a detection unit configured to detect whether the device main body is in a running state,
wherein the third switch is opened when the first switch and the second switch are short-circuited and the device main body is in the running state.

7. The mobile X-ray imaging device according to claim 1, wherein the third switch is opened after the main body controller receives a third switch opening permission signal from the DR unit controller.

\* \* \* \* \*